United States Patent [19]

Fauran et al.

[11] 4,048,164
[45] Sept. 13, 1977

[54] N'-SUBSTITUTED DERIVATIVES OF 4'-(N-PIPERAZINYLMETHYL)SPIRO DIBENZOCYCLOHEPTADI- (OR TRI-) ENE-5,2'-DIOXOLANE(1',3')

[75] Inventors: Claude P. Fauran; Guy M. Raynaud; Michel J. Turin, all of Paris; Janine M. Thomas, Neuilly (Hauts de Siene), all of France

[73] Assignee: Delalande S.A., Courbevoie, France

[21] Appl. No.: 541,609

[22] Filed: Jan. 16, 1975

Related U.S. Application Data

[63] Continuation-in-part of Ser. No. 263,409, June 16, 1972, abandoned.

[30] Foreign Application Priority Data

June 18, 1971 France .................................. 69.22226

[51] Int. Cl.² ........................................... C07D 413/14
[52] U.S. Cl. ................. 544/121; 424/248.56; 260/268 TR
[58] Field of Search .............. 260/247.5, 268, 247.5 D

[56] References Cited

U.S. PATENT DOCUMENTS

| | | | |
|---|---|---|---|
| 3,687,965 | 8/1972 | Fauran et al. | 260/307 |
| 3,696,100 | 10/1972 | Raynaud et al. | 260/247.5 |
| 3,726,900 | 4/1973 | Fauran et al. | 260/340.9 |
| 3,845,046 | 10/1974 | Fauran et al. | 260/340.9 |

Primary Examiner—Henry R. Jiles
Assistant Examiner—R. W. Ramsuer
Attorney, Agent, or Firm—Woodhams, Blanchard and Flynn

[57] ABSTRACT

Compounds of the formula

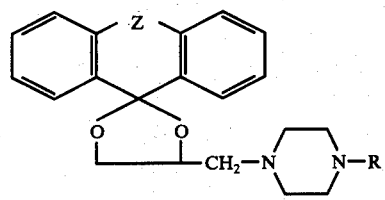

wherein Z is —CH$_2$CH$_2$— or —CH=CH—, and R is methyl, ethoxycarbonylmethyl or

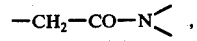

wherein

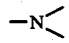

is methylamino, n-propylamino, isopropylamino, dimethylamino, di(n-propyl)amino, morpholino, pyrrolidino or hexamethyleneimino. The compounds are prepared by reacting piperazine substituted with R, with 4'-bromomethyl-5,2'-spiro-dibenzocycloheptadi- (or tri)ene-(1',3') dioxolan. The compounds possess cough-suppressing, spasmolytic, analgesic, respiratory analeptic, hypotensive, vasodilatory, antiarythmic, antiulcerous, antihistamine, sedative, anti-inflammatory, diuretic and antiserotonine properties.

3 Claims, No Drawings

N'-SUBSTITUTED DERIVATIVES OF 4'-(N-PIPERAZINYLMETHYL)SPIRO DIBENZOCYCLOHEPTADI- (OR TRI-) ENE-5,2'-DIOXOLANE(1',3')

CROSS-REFERENCE TO RELATED APPLICATION

This application is a continuation-in-part of Ser. No. 263,409, filed June 16, 1972, now abandoned.

The present invention relates to new N'-substituted derivatives of 4'-(N-piperazinylmethyl)spiro dibenzocycloheptadi- (or tri-) ene-5,2'-dioxolane (1',3').

The compounds have the formula:

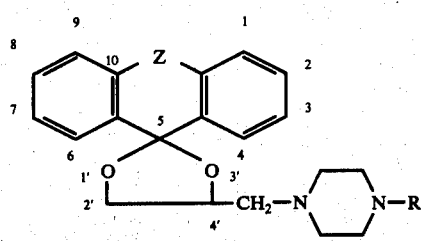

(I)

in which:
Z represents a —CH$_2$—CH$_2$—group or a —CH=CH—group, and
R represents:
methyl, or
ethoxycarbonylmethyl, or
methylaminocarbonylmethyl, propylaminocarbonylmethyl, isopropylaminocarbonylmethyl, dimethylaminocarbonylmethyl, dipropylaminocarbonylmethyl, morpholinocarbonylmethyl, pyrrolidinocarbonylmethyl or hexamethyleneiminocarbonylmethyl, that is, compounds in which R is

wherein

is methylamino, n-propylamino, isopropylamino, dimethylamino, di(n-propyl)amino, morpholino, pyrrolidino or hexamethyleneimino.

The compounds are prepared reacting the bromomethyl-4'-spiro dibenzocycloheptadi- (or tri-)ene-5,2'-dioxolane (1',3') having as formula (II)

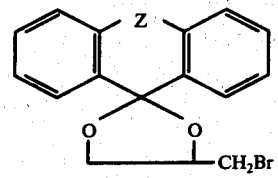

on a monosubstituted piperazine having as formula:

(III)

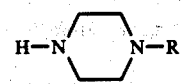

in which R and Z have the same meaning as in formula (I).

The compound of formula (II) in itself obtained by reacting, in the presence of tin tetrachloride, epibromhydrin having the formula (IV)

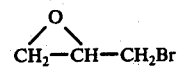

on dibenzo (a-d) cycloheptadi- (or tri-)enone having the formula:

(V)

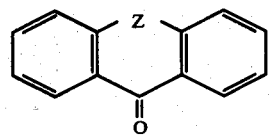

The following preparation is given as a non-limiting example to illustrate the process.

EXAMPLE

4'-N'-(2",3"-dihydroxy 1"-propyl) N-piperazinyl methyl spiro dibenzo (a,d) cycloheptadiene-5 : 2'dioxolane (1',3') dimaleate. Code number : 70405

In 300 ml of CHCl$_3$ are dissolved 62 g of dibenzocycloheptadienone and 11 g of SnCl$_4$. This mixture is cooled to 5° C., then 50 g of epibromhydrin in solution in 100 ml of CHCl$_3$ are slowly introduced; after 3 hours of contact at the same temperature caustic soda lye is added to alkalize the mixture, then the organic phase is washed several times with water. After concentration, a crude product is obtained which is recrystallized in isopropyl alcohol. After recrystallization 92 g of 4'-bromomethyl spiro dibenzo (a,d) cycloheptadiene-5 : 2'-dioxolane (1',3') are obtained.

In 300 ml of toluene are dissolved 34.5 g of the bromomethylated derivative thus prepared, then 16 g of sodium carbonate and 32 g of N-2,3 dihydroxy 1-propyl piperazine are introduced. It is refluxed while stirring for 8 hours, then, after cooling, 500 ml of water and 300 ml of ethyl acetate are added. After decantation, the organic solution is concentrated. The oily crude product obtained is treated in acetone with 23 g of maleic acid. The dimaleate obtained is separated by filtration and recrystallized in ethanol.

Melting point : 179° C.
Yield : 45%

The titre of the compound obtained, as potentiographically determined, is 99%. The water content, as determined by K. Fischer's method is 0.55%. The compounds listed in the following Table I were prepared by the same method of operation.

EXAMPLE 2

-4'-[N'-(di-n-propylaminocarbonylmethyl)N-piperazinyl methyl]spiro[dibenzo(a,d)cycloheptatriene-5:2'dioxolane (1',3')]dimaleate To a solution of 0.4 mole of N-[di-n-propylaminocarbonylmethyl] piperazine in 500 ml of toluene, under reflux, there is added 0.2 mole of sodium carbonate and then 0.2 mole of bromomethyl-4'-spiro[dibenzocycloheptatriene-5:2' dioxolane (1',3']. Reflux is maintained for 8 hours. After cooling, 500 ml of water and 300 ml of ethyl acetate are added. After decantation, the organic solution is concentrated. The crude product is recrystallized from isopropyl ether. To a solution of 0.12 mole of the thus-obtained compound, in 700 ml of acetone, is added 0.24 mole of maleic acid in 150 ml of acetone. The crude dimaleate thus obtained is separated by filtration and is recrystallized from 400 ml of ethanol.

TABLE I

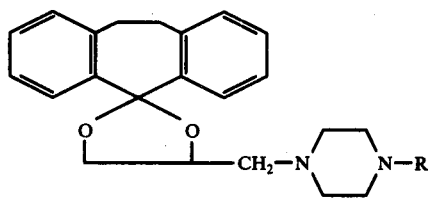

| Code number | R | Empirical formula | Molecular weight | Melting point | yield | Calculated C | Calculated H | Calculated N | Found C | Found H | Found N |
|---|---|---|---|---|---|---|---|---|---|---|---|
| 70358 | —CH$_3$ | C$_{31}$H$_{36}$N$_2$O$_{10}$ | 596.61 | 202° C | 50% | 62.40 | 6.08 | 4.70 | 62.41 | 6.03 | 4.87 |
| 70365 | —CH$_2$COOC$_2$H$_5$ | C$_{34}$H$_{40}$N$_2$O$_{12}$ | 668.67 | 156° C | 69% | 61.07 | 6.03 | 4.19 | 60.96 | 5.99 | 4.30 |
| 70347 | —CH$_2$—CO—N(H)(CH(CH$_3$)$_2$) | C$_{35}$H$_{43}$N$_3$O$_{11}$ | 681.71 | 188° C | 39% | 61.66 | 6.36 | 6.16 | 61.58 | 6.31 | 6.30 |
| 70357 | —CH$_2$—CO—N(morpholino) | C$_{36}$H$_{43}$N$_3$O$_{12}$ | 709.72 | 198° C | 48% | 60.92 | 6.11 | 5.92 | 60.84 | 6.00 | 6.10 |
| 70339 | —CH$_2$—CO—N(pyrrolidino) | C$_{36}$H$_{43}$N$_3$O$_{11}$ | 693.72 | 174° C | 68% | 62.32 | 6.25 | 6.06 | 62.41 | 6.23 | 6.26 |
| 70374 | —CH(C$_6$H$_5$)$_2$ | C$_{39}$H$_{40}$N$_2$O$_6$ | 632.72 | 209° C | 31% | 74.03 | 6.37 | 4.43 | 74.15 | 6.25 | 4.63 |

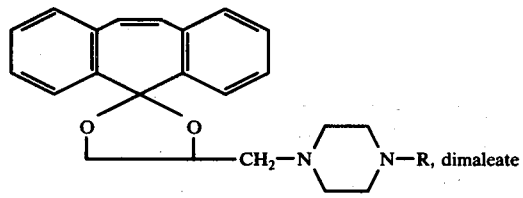

| Code number | R | Empirical formula | Molecular weight | Melting point | yield | Calculated C | Calculated H | Calculated N | Found C | Found H | Found N |
|---|---|---|---|---|---|---|---|---|---|---|---|
| 72143 | —CH$_3$ | C$_{31}$H$_{34}$N$_2$O$_{10}$ | 594.59 | 176° C | 58% | 62.62 | 5.76 | 4.71 | 62.50 | 5.98 | 4.91 |
| 72196 | —CH$_2$—CHOH—CH$_2$OH | C$_{33}$H$_{38}$N$_2$O$_{12}$ | 654.65 | 167° C | 44% | 60.54 | 5.85 | 4.28 | 60.34 | 5.95 | 4.48 |
| 72188 | —CH$_2$—CONH—CH$_3$ | C$_{33}$H$_{37}$N$_3$O$_{11}$½H$_2$O | 660.65 | 106° C | 23% | 59.99 | 5.80 | 6.36 | 59.81 | 5.71 | 6.52 |
| 72134 | —CH$_2$—CO—NH—CH(CH$_3$)$_2$ | C$_{35}$H$_{41}$N$_3$O$_{11}$ | 679.70 | 170° C | 79% | 61.84 | 6.08 | 6.18 | 61.93 | 6.23 | 6.37 |
| 7251 | —CH$_2$—CO—N(CH$_3$)$_2$ | C$_{34}$H$_{39}$N$_3$O$_{11}$ | 665.67 | 174° C | 70% | 61.34 | 5.91 | 6.31 | 61.14 | 5.88 | 6.42 |

TABLE I-continued

| Code | Group | Formula | MW | mp | Yield | %C | %H | %N | %C | %H | %N |
|---|---|---|---|---|---|---|---|---|---|---|---|
| 7204 | $-CH_2-CO-N\begin{pmatrix}C_3H_7\,(\eta)\\C_3H_7\,(\eta)\end{pmatrix}$ | $C_{30}H_{39}N_3O_3$*<br>$C_{38}H_{47}N_3O_{11}$ | 489.63<br>721.78 | 107° C<br>148° C | 78%<br>81% | 73.59<br>63.23 | 8.03<br>6.56 | 8.58<br>5.82 | 73.52<br>65.06 | 8.12<br>6.48 | 8.72<br>5.80 |
| 71562 | $-CH_2-CO-N\langle\rangle$ (pyrrolidine) | $C_{36}H_{41}N_3O_{11}$ | 691.71 | 160° C | 70% | 62.51 | 5.97 | 6.08 | 62.51 | 6.01 | 5.93 |
| 71564 | $-CH_2-CO-N\langle\rangle O$ (morpholine) | $C_{28}H_{33}N_3O_4$*<br>$C_{36}H_{41}N_3O_{12}$ | 475.56<br>707.71 | 155° C<br>153° C | 83%<br>66% | 70.71<br>61.09 | 6.99<br>5.84 | 8.84<br>5.94 | 70.83<br>60.89 | 7.03<br>5.88 | 8.75<br>5.85 |
| 72176 | $-CH_2-CO-N\langle\rangle$ (hexamethyleneimine) | $C_{38}H_{45}N_3O_{11}$ | 719.76 | 154° C | 49% | 63.41 | 6.22 | 5.84 | 63.33 | 6.34 | 5.94 |
| 72142 | $-CH_2-CONHC_3H_7\,(\eta)$ | $C_{35}H_{41}N_3O_{11}$ | 679.70 | 165° C | 41% | 61.84 | 6.08 | 6.18 | 61.81 | 6.21 | 6.30 |

*base

The compounds of formula I were studied with laboratory animals and showed antiserotonine, anti-cough, spasmolytic, analgesic and respiratory analeptic, hypotensive, vasodilatory, antiarythmic, antiulcerous, antihistamine, sedative, anti-inflammatory and diuretic properties. The compounds of formula I do not exhibit anti-depressive properties.

1. ANTI-COUGH PROPERTIES

The compounds of formula (I) administered intravenously and intraduodenally reduced the cough caused by stimulation of the upper laryngeal nerve in an anaesthetized cat. The results obtained with a certain number of these compounds are given in the following Table II:

Table II

| Code number of | Dose | Reduction of cough | |
|---|---|---|---|
| compound tested | administered | intensity | duration |
| 70357 | 2 mg/kg/IV | 100% | 20 mm |
| 70358 | 25 mg/kg/ID | 100% | >60 mm |
| 70356 | 2 mg/kg/IV | 100% | 90 mm |
| 70339 | 1 mg/kg/IV | 100% | 20 mm |
| 70347 | 1 mg/kg/IV | 80% | 20 mm |
| 70405 | 100 mg/kg/ID | 100% | 60 mm |

2. SPASMOLYTIC PROPERTIES

Compounds of formula I, introduced in the survival medium, are capable of opposing the contacting action of barium chloride on the isolated duodenum of a rat. This activity is determined either by taking papaverine as the standard or by calculating the $DE_{50}$ of the compound tested. The results obtained with certain of these compounds are given in the following Tables III and IV.

Table III

| Code number of compound tested | Spasmolytic activity |
|---|---|
| 70357 | 1.5 × papaverine |
| 70358 | 1.5 × papaverine |
| 70365 | 3 × papaverine |
| 70339 | 1 × papaverine |
| 70347 | 1.5 × papaverine |

Table IV

| Code number of compound tested | $DE_{50}$ μg/ml |
|---|---|
| 72143 | 3.75 |
| 72196 | 0.25 |
| 7251 | 3.50 |

Table IV-continued

| Code number of compound tested | $DE_{50}$ μg/ml |
|---|---|
| 7204 | 2.50 |
| 71564 | 2.50 |
| 72176 | 3.50 |
| 72142 | 2.50 |

3. ANALGESIC PROPERTIES

The compounds of formula (I) administered orally to a mouse are capable of reducing the number of painful stretchings following the intraperitoneal injection of acetic acid.

By administering 100 mg/kg/PO of different compounds of formula (I) the results shown in the following Table V are obtained.

Table V

| Code number of compound tested | Percentage reduction in the number of painful stretchings (%) |
|---|---|
| 70358 | 43 |
| 70365 | 75 |
| 70347 | 70 |
| 70339 | 75 |
| 72196 | 45 |
| 72188 | 60 |
| 7251 | 50 |
| 7204 | 70 |
| 71562 | 47 |
| 72142 | 70 |

4. RESPIRATORY ANALEPTIC PROPERTIES

The compounds of formula (I) administered intravenously to an anaesthetized guinea pig are capable of opposing respiratory depression caused by morphine. As an example, with a dose of 5 mg/kg/IV, compound 70358 increased respiratory frequency by 65%.

5. HYPOTENSIVE PROPERTIES

Administered intravenously to an anaesthetized rat, the compounds of formula (I) cause a lowering of arterial pressure. The results obtained with a certain number of these compounds are shown in the following Table VI.

Table VI

| Code number of | Dose | Reduction of arterial pressure | |
|---|---|---|---|
| compound tested | administered | intensity | duration |
| 70374 | 2 mg/kg/IV | 35 % | 20 mm |

Table VI-continued

| Code number of compound tested | Dose administered | Reduction of arterial pressure | |
|---|---|---|---|
| | | intensity | duration |
| 70339 | 1 mg/kg/IV | 80 % | >30 mm |
| 70347 | 2 mg/kg/IV | 50 % | >30 mm |
| 70405 | 2 mg/kg/IV | 40 % | >60 mm |

6. ANTIINFLAMMATORY PROPERTIES

These properties bring about a reduction of the local edema, caused by injecting a rat under the plantar with a phlogogenic agent such as carraghenine, following oral administration of compounds of formula (I). As examples the results obtained with a few of the compounds of formula (I) are given in the following Table VII.

Table VII

| Code number of compound tested | Dose administered (mg/kg/PO) | Percentage reduction of the edema (%) |
|---|---|---|
| 72143 | 30 | 70 |
| 72196 | 100 | 70 |

7. VASODILATORY PROPERTIES

The compounds of formula (I) are able to increase the flow in the coronary vessels of the isolated heat of a guinea pig when they are added to the perfusion liquid of this organ. As an example, by adding 0.5 µg/ml of the compound code number 71562 to the perfusion liquid of the isolated heart of a guinea pig, a 45% increase in the flow of the coronary vessels was observed.

8. ANTIARYTHMIC PROPERTIES

Administered intraperitoneally, the compounds of formula (I) are able to protect the mouse against ventricular fibrillations caused by inhaling chloroform. As examples, the results obtained with different compounds of formula (I) are listed in the following Table VIII.

Table VIII

| Code number of compound tested | Antagonism to fibrillations caused by chloroform with a mouse $DE_{50}$ (mg/kg/IP) |
|---|---|
| 72195 | 60 |
| 72188 | 38 |
| 72134 | 65 |
| 7251 | 100 |
| 71562 | 125 |
| 71564 | 200 |
| 72176 | 100 |
| 72142 | 85 |
| 7204 | 100 |

9. ANTIULCEROUS PROPERTIES

Compounds of formula (I) administered intraduodenally reduce the size of gastric ulcers caused in a rat by ligature of the pylorus (Shay ulcers). As examples, the intradeuodenal administration of 50 mg/kg of the compounds of code numbers 72143 and 7251 bring about a 70% and 65% reduction respectively of the Shay ulcer.

10. ANTIHISTAMINE PROPERTIES

The compounds of formula (I) introduced in the survival medium are able to oppose the contracting action of histamine on the isolated ileum of a guinea pig. This activity is calculated by the DE50 of the tested compounds. The results obtained for different compounds of formula (I) are listed in Table IX below.

Table IX

| Code number of compound tested | Antihistamine activity $DE_{50}$ (µg/ml) |
|---|---|
| 72143 | 0.25 |
| 72196 | 1 |
| 72188 | 1 |
| 72134 | 1 |
| 72176 | 0.5 |
| 72142 | 0.6 |

11. SEDATIVE PROPERTIES

The compounds of formula (I) administered orally to a mouse reduce the number of explorations in the escape enclosure. As examples, the administration of 100 mg/kg/PO of the compounds of code numbers 71562 and 72142 bring about a 40% reduction in the number of explorations in the escape enclosure in each case.

12. DIURETIC PROPERTIES

The compounds of formula (I) administered orally to a mouse simultaneously with a volume of 1 ml of sodium chloride isotonic solute per 25 g of body weight are able to cause an increase of the volume of urine given compared with controls, this volume being measured for the 4 hours following administration. As examples, the results obtained with different compounds of formula (I) are given in Table X below.

Table X

| Code number of compound tested | Dose administered (mg/kg/PO) | Percentage increase in urinary elimination |
|---|---|---|
| 72 143 | 25 | 70 |
| 72 196 | 12.5 | 40 |
| 72 188 | 25 | 40 |
| 72 134 | 50 | 55 |
| 7 251 | 50 | 45 |
| 71 562 | 50 | 70 |
| 71 564 | 12.5 | 50 |
| 72 142 | 50 | 55 |

13. ANTISEROTTONINE PROPERTIES

The compounds of formula (I) possess a particularly significant antiserotonine property. This property is exhibited in in vivo tests, i.e. antagonism against bronchoconstrictions provoked by intravenous injection of serotonine to guinea pigs (Konzett and Rossler test), and in in vitro tests, i.e. reduction of the contractions of the isolated fundus of rats and the isolated tied uterus, provoked by serotonine.

For purposes of comparison, compounds of the formula (I) were compared, as to their antiserotonine properties, with a representative sampling of compounds disclosed in U.S. Pat. No. 3,726,900. The comparison compounds tested have the formula

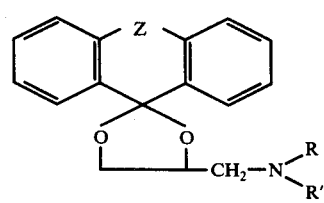

The specific compounds tested were as follows:

| Code No. | Z | 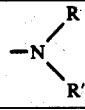 -N<R/R' |
|---|---|---|
| 69257 | —CH₂—CH₂— | —N(CH₃)₂ |
| 70301 | —CH=CH— | |
| 70312 | —CH=CH— | —N(CH₃)₂ |
| 70315 | —CH=CH— |  |

The results of comparative tests carried out under the same conditions were as follows:

Table XI

| | Antiserotonine Properties | | | Antagonisms against contractions of: | |
|---|---|---|---|---|---|
| Code Number of compounds tested | Test of Konzett and Rossler DE$_{50}$ (mg/kg/I.V.) | LD$_{50}$ (mice) (mg/kg/P.O) | $\frac{DE_{50}}{LD_{50}} \times 10^5$ | Tied uterus DE$_{50}$ (g/ml) | Fundus of rat DE$_{50}$ (g/ml) |
| Compounds of the invention | | | | | |
| 70.358 | — | 1000 | — | — | 4.94 |
| 70.365 | 0.6 | 1250 | 48 | 6 | 3.27 |
| 70.357 | 0.005 | 1300 | 0.38 | 0.005 | 0.54 |
| 70.339 | 0.1 | 1200 | 8.3 | 0.002 | 0.67 |
| 70.347 | 0.5 | 1200 | 41 | 0.02 | 1.78 |
| 72.143 | — | 300 | — | — | 4.09 |
| 72.196 | — | 1100 | — | — | 3.51 |
| 72.188 | 0.25 | 1100 | 25 | — | 2.61 |
| 72.142 | 0.6 | 1650 | 36 | — | 2.12 |
| 72.134 | — | 1200 | — | — | 1.72 |
| 72.51 | — | >2000 | — | — | 2.61 |
| 72.04 | — | 1900 | — | — | 0.07 |
| 71.562 | — | 2000 | — | — | 0.1 |
| 71.564 | 0.05 | 3500 | 14 | 0.001 | 0.74 |
| Compounds of U.S. Pat. No. 3 726 900 | | | | | |
| 69.257 | 0.40 | 550 | 72 | — | — |
| 70.301 | 0.40 | 425 | 94 | — | — |
| 70.312 | 0.43 | 480 | 89 | — | — |
| 70.315 | 1.40 | 700 | 200 | — | — |

14. ANTI-DEPRESSIVE PROPERTIES

The compounds of formula (I) demonstrate no activity when tested by the two principal screening tests for antidepressive activity, namely, opposing the ptosis caused by the intravenous injection of reserpine and potentialization of the lethal effect of yohimbine. In this regard, the compounds of formula I differ unexpectedly from the compounds of U.S. Pat. No. 3,726,900, as shown by comparative testing.

The results of these comparative tests were as follows:

Table XII

| | Anti-Depressive Properties | | |
|---|---|---|---|
| Code No. compounds tested | LD$_{50}$ mg/kg/P.O. | Antagonism against ptosis caused by reserpine | Potentialization of lethal effect of yohimbine |
| 70.358 | 1000 | Inactive at 100 mg/kg/PO | 40% at 100 mg/kg/PO |
| 70.365 | 1250 | Inactive at 100 mg/kg/PO | Inactive at 100 mg/kg/PO |
| 70.357 | 1300 | Inactive at 100 mg/kg/PO | Inactive at 100 mg/kg/PO |
| 70.339 | 1200 | Inactive at 100 mg/kg/PO | Inactive at 100 mg/kg/PO |
| 70.347 | 1200 | Inactive at 100 mg/kg/PO | Inactive at 100 mg/kg/PO |
| 70.374 | >2000 | Inactive at 100 mg/kg/PO | Inactive at 100 mg/kg/PO |
| 72.143 | 300 | Inactive at 50 mg/kg/PO | — |
| 72.142 | 1650 | Inactive at 100 mg/kg/PO | 40% at 100 mg/kg/PO |
| 72.188 | 1100 | Inactive at 50 mg/kg/PO | — |
| 72.134 | 1200 | Inactive at 50 mg/kg/PO | — |
| 72.51 | >2000 | Inactive at 50 mg/kg/PO | — |
| Compounds of U.S. Pat. No. 3 726 900 | | | |
| 69.257 | 550 | DE$_{50}$: 35 mg/kg/PO | DE$_{50}$: 10 mg/kg/PO |
| 70.312 | 480 | DE$_{50}$: 13 mg/kg/PO | DE$_{50}$: 46 mg/kg/PO |
| 70.315 | 700 | 45% at 75 mg/kg/PO | — |

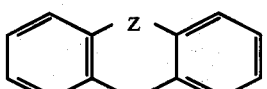

The anti-depressive properties of additional analog compounds were tested by the same tests. In these tests, the comparison compounds had the formula

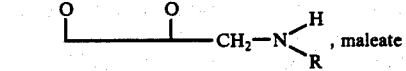

The specific compounds tested and the test results are indicated in Table XIII.

Table XIII

| | Anti-Depressive Properties | | |
|---|---|---|---|
| | $LD_{50}$ mg/kg/PO | Antagonism against ptosis caused by reserpine ($DE_{50}$ mg/kg/PO) | Potentialization of lethal effect of yohimbine |
| —Z— = —$CH_2$—$CH_2$— | | | |
| R | | | |
| $CH_3$ | 850 | 60 | 50 mg/kg/PO |
| $C_4H_9$ (s) | 900 | 45 | ≈40% at 50 mg/kg/PO |
| $C_2H_5$ | 550 | ≈50 | — |
| —Z— = —CH = CH— : | | | |
| R | | | |
| $CH_3$ | 750 | 25 | 29 mg/kg/PO |
| $C_2H_5$ | 375 | 70 | 60% at 50 mg/kg/PO |
| $C_3H_7$ (i) | 550 | 20% at 50 mg/kg/PO | — |

As is shown by the preceding results and by those given in Table XIV below, the difference between pharmacologically active doses and lethal doses is sufficiently great to allow the use of compounds of formula (I) in therapeutics.

Table XIV

| Code numbers of compounds tested | Dose administered (mg/kg/PO) | Percentage of mortality with mice (%) |
|---|---|---|
| 70 357 | 1300 | ≈50 |
| 70 358 | 1000 | ≈50 |
| 70 365 | 1250 | ≈50 |
| 70 374 | 2000 | 0 |
| 70 339 | 1200 | ≈50 |
| 70 347 | 1200 | ≈50 |
| 70 405 | 1600 | ≈50 |
| 72 143 | 300 | ≈50 |
| 72 196 | 1100 | ≈50 |
| 72 188 | 1100 | ≈50 |
| 72 134 | 1200 | ≈50 |
| 7 251 | 2000 | 0 |
| 7 204 | 1900 | ≈50 |
| 71 562 | 2000 | ≈50 |
| 71 564 | 3500 | ≈50 |
| 72 176 | 3400 | ≈50 |
| 72 142 | 1650 | ≈50 |

The compounds of formula I are recommended in the treatment of coughs, vascular and visceral spasms, pains, respiratory depression, hypertension, circulatory insufficiencies, cardiac arythmia, gastroduedenal ulcers, allergies and edemas.

They are administered orally in the form of tablets, pills or gelules containing 25 to 300 mg of active principle (3 to 5 a day) and in the form of a syrup dosed with 0.1 to 2% (3 to 6 soup-spoonfuls a day), parenterally in the form of phials containing 25 to 125 mg of active principle (1 to 3 a day) and rectally in the form of suppositories containing 50 to 200 mg of active principle (1 to 2 a day).

The embodiments of the invention in which an exclusive property or privilege is claimed are defined as follows:

1. A compound of the formula

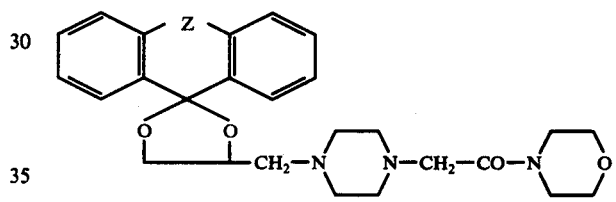

wherein Z is —$CH_2CH_2$— or —CH=CH—, and the pharmacologically acceptable acid addition salts thereof.

2. A compound as claimed in claim 1 in which Z is —$CH_2CH_2$—.

3. A compound as claimed in claim 1 in which Z is —CH=CH—.

* * * * *

UNITED STATES PATENT AND TRADEMARK OFFICE
CERTIFICATE OF CORRECTION

PATENT NO. : 4 048 164

DATED : September 13, 1977

INVENTOR(S) : Claude P. Fauran; Guy M. Raynaud; Michel J. Turin and Janine M. Thomas It is certified that error appears in the above-identified patent and that said Letters Patent are hereby corrected as shown below:

Under "Foreign Application Priority Data" please change "69.22226" to ---71.22226---.

Signed and Sealed this

Third Day of January 1978

[SEAL]

Attest:

RUTH C. MASON
*Attesting Officer*

LUTRELLE F. PARKER
*Acting Commissioner of Patents and Trademarks*